(12) United States Patent
Bolz

(10) Patent No.: US 6,763,697 B2
(45) Date of Patent: Jul. 20, 2004

(54) METHOD AND DEVICE FOR OPERATING A LINEAR LAMBDA PROBE

(75) Inventor: Stephan Bolz, Pfatter (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/320,208

(22) Filed: Dec. 16, 2002

(65) Prior Publication Data

US 2003/0079521 A1 May 1, 2003

Related U.S. Application Data

(63) Continuation of application No. PCT/DE01/02139, filed on Jun. 8, 2001.

(30) Foreign Application Priority Data

Jun. 16, 2000 (DE) .......................................... 100 29 831

(51) Int. Cl.[7] ............................................ G01M 15/00
(52) U.S. Cl. ........................ 73/23.2; 73/23.31; 73/31.05
(58) Field of Search ............................... 73/23.2, 23.31, 73/31.05

(56) References Cited

U.S. PATENT DOCUMENTS

| | | | |
|---|---|---|---|
| 4,135,381 A | 1/1979 | Sherwin | 73/23 |
| 5,106,481 A | 4/1992 | Rankin et al. | 204/426 |
| 5,173,167 A | 12/1992 | Murase et al. | 204/426 |
| 6,073,083 A | 6/2000 | Schnaibel et al. | 702/65 |
| 6,447,660 B2 | 9/2002 | Amtmann et al. | 204/425 |

OTHER PUBLICATIONS

Datasheet CJ110, Robert Bosch GmbH, Sep. 1998 "Integrated Circuit for Continuous Lambda Regulation," pp. 1–6.

Primary Examiner—Daniel S. Larkin
(74) Attorney, Agent, or Firm—Baker Botts L.L.P.

(57) ABSTRACT

The oxygen concentration lambda in the exhaust gas of an internal combustion engine is determined by establishing the average of the upper value OW and the lower value UW of the square-wave sum voltage Vsum corresponding to the difference DELTA Vs between the Nernst voltage Vs and the reference voltage Vref and converting this into a proportional pump current Ip which produces a Rc lambda—proportional voltage at the calibration resistor. The difference between the upper value OW and lower value UW of the sum voltage Vsum is used as a temperature measurement voltage Vri for regulating the temperature of the probe.

15 Claims, 4 Drawing Sheets

METHOD AND DEVICE FOR OPERATING A LINEAR LAMBDA PROBE

CROSS REFERENCE TO RELATED APPLICATION

This application is a continuation of copending International Application No. PCT/DE01/02139 filed Jun. 8, 2001, which designates the United States. This application also claims foreign priority benefits under 35 U.S.C. § 119 of German application DE 10029831.1 filed Jun. 16, 2000.

BACKGROUND OF THE INVENTION

The invention relates to a device and a method for operating a linear lambda probe of an internal combustion engine.

A linear lambda probe is used to determine the oxygen concentration in the exhaust gas of an internal combustion engine. It has two pairs of electrodes and a measuring chamber which is connected to the exhaust gas stream via a diffusion barrier. The first pair of electrodes (measuring electrodes) are arranged between the measuring chamber and air and are used to measure the oxygen concentration in the measuring chamber. The second pair of electrodes (pump electrodes) are arranged between the measuring chamber and the exhaust gas stream. This permits oxygen ions to be pumped out of the measuring chamber, or into it, when a current Ip with a corresponding polarity is applied.

In this way it is possible to generate a dynamic equilibrium between the flow of oxygen through the diffusion barrier and the flow of oxygen ions through the pair of pump electrodes. The oxygen concentration in the measuring cell which can be determined using the measuring electrodes is suitable here as a regulating criterion. A preferred value is, for example, 450 mV for $\lambda=1$. The pump current Ip which flows in this case is a measure of the oxygen concentration in the exhaust gas (and also for $\lambda$ after numerical conversion).

Hitherto, the application of the linear lambda probe has been restricted to the nonsupercharged, stoichiometric mode of operation (Pa=1 bar, $\lambda=1$) of the engine. Correspondingly, only small pump currents are necessary to maintain the equilibrium ($\lambda=1$) in the measuring cell ($|IP|<\sim2.5$ mA).

For lean engines, an operating mode up to $\lambda=4$ is provided, which requires a drastically increased pump current Ip. When operating in a supercharged (turbo) engine, an exhaust gas pressure of up to 2 bar is produced. The pressure sensitivity of the probe leads to a further increase in the maximum necessary pump current of up to ±12 mA.

The dynamic resistance of the diffusion barrier has a temperature dependence which leads to errors in the transmission ratio. This is countered by measuring the probe temperature and regulating it by means of a heating element which is installed in the probe. For reasons of cost, a separate thermal element is dispensed with here. Instead, the highly temperature-dependent internal resistance Ris of the probe is measured.

A customary measuring method for determining the internal resistance Ris of the probe is to apply to the probe terminal Vs+ a measuring signal M formed from a square wave alternating current—for example 500 $\mu$Ass (peak-to-peak) with a frequency fm of, for example, 3 kHz. This alternating current brings about an alternating voltage of 500 $\mu$Ass*100 $\Omega$=50 mVss with an internal resistance Ris of the probe of 100 $\Omega$, for example. This alternating voltage is amplified in an amplifier, for example by the factor ten, and then rectified. The direct voltage Vri which has been produced in this way can be used and further processed as a measure of the probe temperature.

A known evaluation circuit is illustrated in FIG. 1 and will be described in more detail below.

This circuit has certain disadvantages:

When the evaluation circuit is supplied with a supply voltage Vcc=5 V which is generally already available, a center voltage Vm of approximately 2.5 V is produced. The voltage chain which is present at the probe is obtained as:

$Vm<|Rc*Ip+Vp|+Vsat$; where

Rc=30 to 100 $\Omega$=overall calibration resistance (manufacturer-dependent),

Vp=−350 to +450 mV; polarization voltage of the pump cell,

Vsat=100 to 200 mV; saturation voltage of the pump current source P; this limits the maximum possible pump current Ip to <10 mA, and therefore does not correspond to the requirements (Ip=±12 mA);

a common mode signal (Vm±2 V) is superimposed on the pump current Ip. The measurement is falsified by up to ±0.3%% by the finite common mode expression of real integrated amplifiers (for example 65 dB);

in addition, the polarization voltage of the pump cell (−350 mV when $\lambda<1$) results in a zero crossover point error $\Delta Ip$ of approximately 5 $\mu$A. As the pump current Ip is the primary measurement signal of the oxygen probe, these errors are included directly in the overall precision of the pump current Ip. This limits the precision of lambda control and thus constitutes a significant problem;

a further fundamental problem of this circuit arrangement is the reciprocal influence between the Nernst voltage Vs and the square wave voltage Vr which is produced from the measurement of the internal resistance. This square wave voltage Vr also appears at the input of the controller R and thus constitutes a control error. The controller will attempt—within the scope of its bandwidth—to compensate this control error. To do this, it changes the pump current Ip, which in turn has effects on Vs. As the pump current Ip is the measurement variable for $\lambda$, the primary probe signal Vs is falsified. In turn the change in Vs is superimposed on the square wave voltage Vr. The effect of this is to cause the signal roof of the square voltage Vr to slope, thus bringing about a considerable amplitude error during the rectification; when EMC interference signals occur there is also a considerable deviation of the actual measured value of the internal resistance Ris.

SUMMARY OF THE INVENTION

The object of the invention is to specify a method for operating a linear lambda probe which makes available values of the pump current Ip which correspond to the requirements set, said method avoiding the described common mode error and significantly improving the precision of the measurement of the pump current so that there is no reciprocal influence between the Nernst voltage Vs and the square wave voltage Vr, and the precision of the measurement of the internal resistance is improved, and which lambda probe remains operational even at a low battery voltage (Vb less than or equal to +6 V). The object of the invention is also to specify a device for carrying out this method.

This object can be achieved according to the invention by a method for operating a linear lambda probe having a first terminal, a second terminal, a third terminal and a fourth terminal, comprising the steps of:

generating a current with a square-wave profile and relatively low frequency from an oscillator signal with a frequency, supplying the current at the first terminal as a measurement signal, tapping a sum voltage between the first and second terminals, whose upper and lower envelopes determine an upper value and a lower value, referring the sum voltage to the difference of a predefined center voltage and a predefined reference voltage, and forming the mean value corresponding to the difference between a Nernst voltage and reference voltage from the upper value and lower value of the sum voltage and converting the mean value into a proportional pump current which brings about, at the calibration resistor of the lambda probe, a voltage drop which is used as a measure of the oxygen concentration.

The step of generating the current can be performed by means of frequency division.

Another method for operating a linear lambda probe of an internal combustion engine having a first terminal, a second terminal, a third terminal and a fourth terminal, comprises the steps of:

a current with a square-wave profile and relatively low frequency which is derived from an oscillator signal with a frequency by means of frequency division is supplied at the first terminal as a measurement signal which brings about a square-wave voltage which drops across the internal resistor of the probe and forms, with the Nernst voltage which can be tapped between the first and second terminals, a sum voltage whose upper and lower envelopes determine an upper value and a lower value, the sum voltage is referred to the difference of a predefined center voltage and a predefined reference voltage, and in order to determine the oxygen concentration in the exhaust gas of the internal combustion engine, the mean value corresponding to the difference between the Nernst voltage and reference voltage is formed from the upper value and lower value of the sum voltage and is converted into a proportional pump current which brings about, at the calibration resistor of the lambda probe, a voltage drop which is used as a measure of the oxygen concentration in the exhaust gas of the internal combustion engine.

In both methods, the difference between the upper value and lower value of the sum voltage can be formed and can be used as a temperature measuring voltage for regulating the temperature of the probe. The temperature measuring voltage can be low-pass filtered. A predefined oxygen reference current can be fed to the reference cell of the lambda probe.

An embodiment according to the present invention can be a device for operating a linear lambda probe of an internal combustion engine, comprising:

an evaluation circuit which is connected to the lambda probe via its terminals, an oscillator which generates an oscillator signal having a frequency, and a measurement signal which is derived therefrom by means of frequency division and has a relatively low frequency which is fed to the first probe terminal, a difference amplifier whose inverting input is connected to the third probe terminal and whose noninverting input is connected to the fourth probe terminal, a controller and a pump current source, a second capacitor in which the lower value of the sum voltage is continuously stored is provided, a third capacitor in which the upper value of the sum voltage is continuously stored is provided, the base points of the second and third capacitors being capable of being connected to the second probe terminal and being connected to the negative pole of a reference voltage, the positive pole of the reference voltage being connected to the positive pole of the center voltage, a decoupling amplifier is connected downstream of each of the other terminals of the second and third capacitors, wherein the outputs of the two decoupling amplifiers are connected to one another by means of a voltage divider whose tap is connected to the noninverting input of the controller, whose output is connected to the fourth probe terminal, and whose inverting input lies at the center voltage and is connected to the noninverting input of the pump current source, the inverting input of the pump current source is connected to the third probe terminal, and the output of the pump current source is connected to the second probe terminal.

A difference amplifier can be provided whose noninverting input is connected to the output of the first decoupling amplifier, whose inverting input is connected to the output of the second decoupling amplifier, and at whose output the temperature measuring voltage can be tapped. A low-pass filter can be connected downstream of the difference amplifier. A first capacitor whose base point can be connected to the second probe terminal via a switch, and to the base points of the second capacitor and third capacitor via a further switch, and whose other terminal is connected to the first probe terminal via a switch, to the other terminal of the second capacitor via a switch, and to the other terminal of the third capacitor via a switch. A switch can be provided via which a predefined oxygen reference current can be fed to the second capacitor, and to the reference cell of the lambda probe via said second capacitor and the first capacitor, as long as the sum voltage is at its upper value, and a switch can be provided via which the predefined oxygen reference current can be fed to the third capacitor, and to the reference cell of the lambda probe via said third capacitor and the first capacitor, as long as the sum voltage is at its lower value. A circuit can be provided for actuating the switches, which circuit alternately connects, with the frequency of the oscillator signal, the first capacitor to the reference cell of the lambda probe via the switches, and to the third capacitor via the switches, as long as the sum voltage is at its upper value, and to the reference cell of the lambda probe via the switches, and to the second capacitor via the switches, as long as the sum voltage is at its lower value.

BRIEF DESCRIPTION OF THE DRAWINGS

An exemplary embodiment of the invention is described in more detail below with reference to a schematic drawing, in which.

DETAILED DESCRIPTION OF THE PREFERRED EMBODIMENTS

Figure 1:
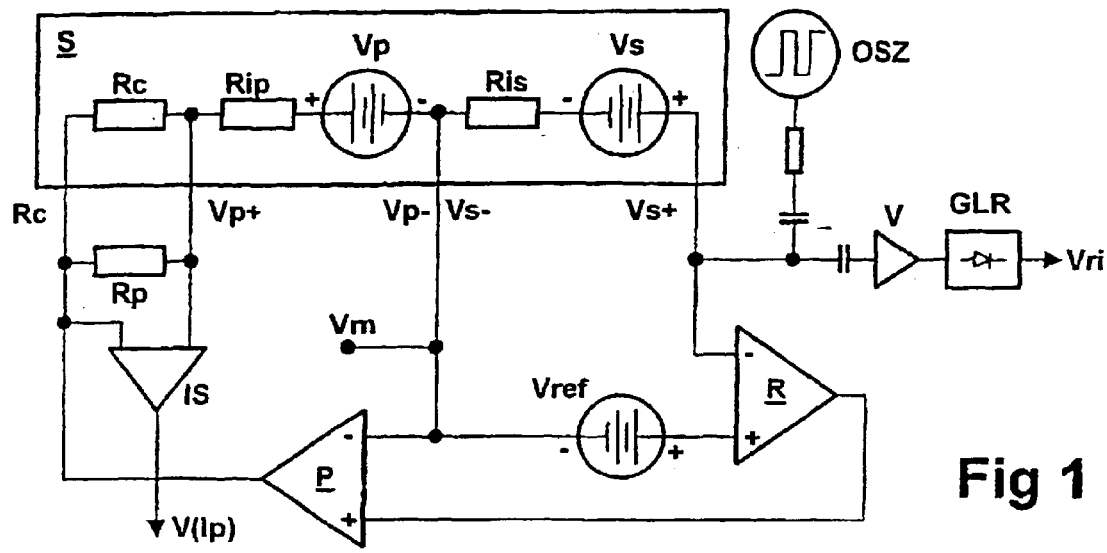
FIG. 1 shows the basic circuitry of a known device for operating a lambda probe.

FIG. 1 shows a basic circuit diagram of the known device for operating a linear lambda probe of an internal combustion-engine in the range $\lambda=1$. The lambda probe S is composed a) of what is referred to as the reference cell, i.e. of the electrodes between the measuring chamber and air, represented in the drawing by the Nernst voltage Vs which can be measured between the electrodes, and the internal resistance Ris of the diffusion barrier between them, b) of what is referred to as the pump cell, i.e. of the electrodes between the measuring chamber and exhaust gas, represented by the pump voltage Vp which drops between them and the (reference) resistance Rip between these electrodes, and c) of the calibration resistor Rc located in the probe plug (not illustrated).

The electrodes are mounted on the ceramic body of the probe. The ceramic material in between the pairs of electrodes is conductive at high temperatures and serves as a solid electrolyte. Lines from a first terminal Vs+, a second terminal Vp−/Vs−, a third terminal Vp+ and a fourth terminal Rc lead out of the probe S and are connected to the evaluation circuit.

The probe heater and its terminals are not illustrated.

The inverting input R− of a differential amplifier R is connected to the first terminal Vs+ of the probe S, its noninverting input R+ is connected to the center voltage Vm (Vm=Vcc/2) via a reference voltage Vref, Vcc (usually 5 V) being the supply voltage of the circuit.

The second probe terminal Vp−/Vs− and the inverting input P− of a pump current source P are also connected to the center voltage Vm, the noninverting input P+ of said pump source current P being connected to the output of the differential amplifier R.

The output of the pump current source P is connected to the fourth input Rc of the probe S.

As the resistor Rc is subjected to considerable environmental stresses owing to its installation position in the probe plug, a further resistor Rp is connected in parallel with it in the controller, at the terminals Vp+ and Rc. This reduces the influence of a tolerance error of Rc on the measuring precision of the pump current Ip.

The difference amplifier R compares the Nernst voltage Vs of the probe S (between the external air and measuring cell) with the reference voltage Vref (450 mV) and generates an output voltage which is proportional to the difference and which is converted, by the pump current source P, into a proportional pump current Ip which flows through the parallel circuit of Rc and Rp and through the pump cell (Rip and Vp) to Vm. The pump current Ip leads to a change in the oxygen concentration in the measuring cell (not illustrated) of the probe S, which in turn results in a change in the Nernst voltage Vs.

The oxygen concentration $\lambda$ is determined in the exhaust gas by measuring the pump current Ip which flows through the parallel circuit of the resistors Rc and Rp and through the pump cell. For this purpose, the voltage drop V(Ip), brought about by the pump current Ip, at the parallel circuit of Rc and Rp is measured by means of a difference amplifier IS.

In this known evaluation circuit, the center voltage Vm=Vcc/2 and the reference voltage Vref are connected to the second terminal Vp−/Vs− of the lambda probe.

In the stable control state ($\lambda=1$) in the measuring cell, the Nernst voltage is Vs=450 mV. There is a state of equilibrium between the flow of oxygen through the diffusion barrier and the flow of oxygen ions, brought about by the pump current Ip. The value of Vp is between 450 mV (air) and −350 mv (rich mixture) here—depending on the oxygen concentration in the exhaust gas.

The maximum range of the output voltage of the pump current source P ranges from approximately 0.1 V to 4.9 V.

In order to measure the internal resistance Ris of the probe, a measurement signal M, for example a square wave alternating current of 500 $\mu$Ass (peak-to-peak) generated in an oscillator OSZ and with a frequency of 3 kHz is applied to the probe S. The signal is fed to the first terminal Vs+ of the lambda probe via a high-impedance resistor and a decoupling capacitor (without a reference symbol in FIG. 1). At the internal resistor Ris, which will be assumed to have for example a resistance of 100 $\Omega$, a square wave voltage Vr=500 $\mu$Ass*100 $\Omega$=50 mVss is then produced. This square wave voltage Vr is amplified in an amplifier V and rectified in a peak value rectifier GLR and can then be supplied to a microprocessor (not illustrated) as a Direct voltage Vri, as a control signal for the temperature control of the lambda probe S. The disadvantages of this circuit have already been presented above.

Figure 2:
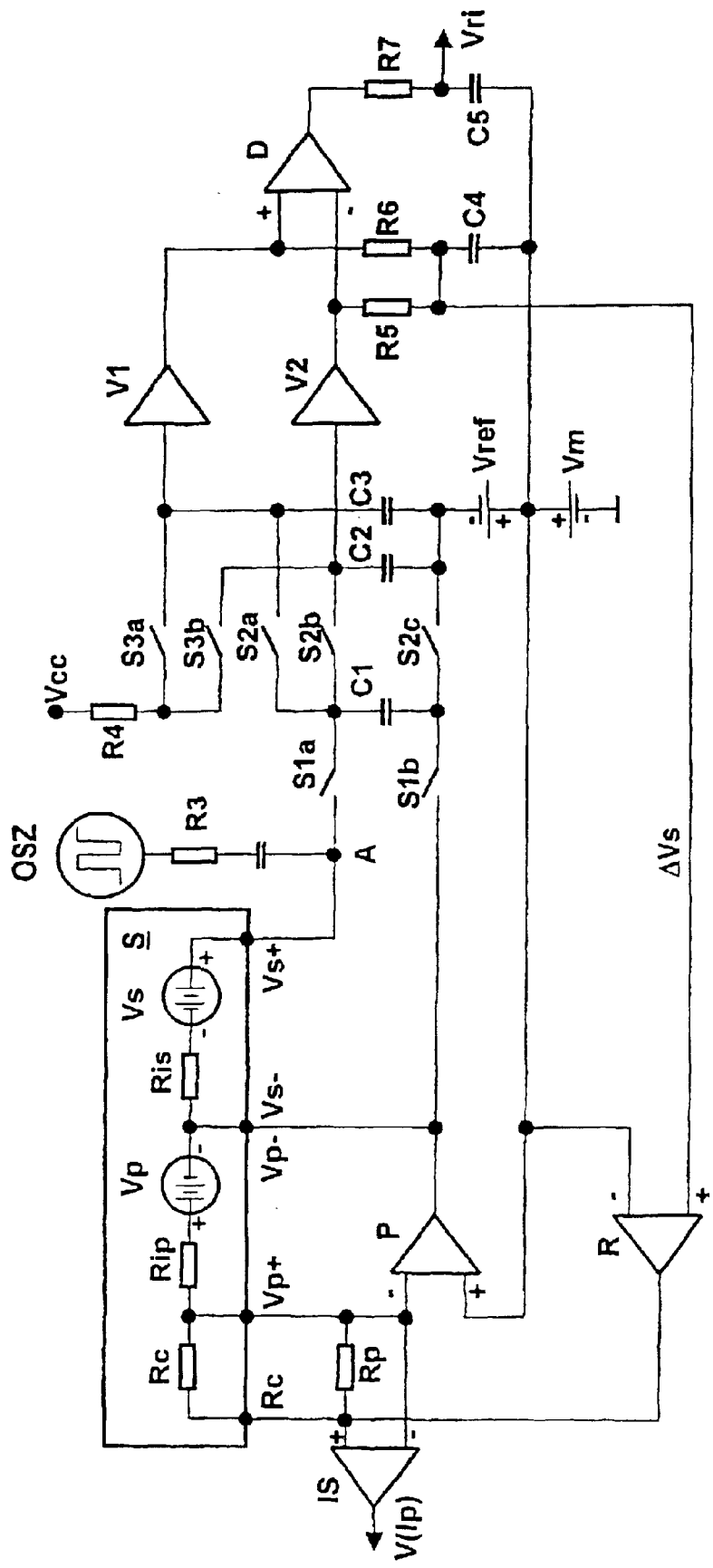
FIG. 2 shows the basic circuitry of a device according to the invention for operating a lambda probe.

FIG. 2 shows a basic circuit of a device according to the invention for operating a lambda probe. The method according to the invention is explained below in more detail by reference to the mode of operation of this device.

The lambda probe S is already known from FIG. 1, as is the resistor Rp connected in parallel with the resistor Rc, and the difference amplifier IS, at whose output a voltage V(Ip) which is proportional to the pump current Ip can be tapped as a measure of the oxygen concentration in the exhaust gas of the internal combustion engine.

The oscillator OSZ generates a square wave oscillator signal OS with a frequency f from which a measurement signal M having the frequency fm is acquired by means of frequency division (fm=f/$2^x$). It will be assumed, for example, that f=48 kHz and fm=3 kHz, where x=4.

The phase angle between the signals OS and M will be assumed here to be such that the measurement signal M switches at half the duration of a low level of the oscillator signal OS (90° phase shift with respect to OS). The measurement signal M is supplied to the probe terminal Vs+.

It will also be assumed that a circuit (illustrated in FIG. 5 and described later) for actuating various switches is also integrated into the oscillator OSZ).

The center voltage Vm is fed to the noninverting input P+ of the pump current source P (composed of an operational amplifier and the parallel circuit of the resistors Rc and Rp which is connected to its noninverting input P−), and its output is connected to the second probe terminal Vp−/Vs−. The output of the pump current source P is also connected via a switch S1$b$ to the base point of a first (transfer) capacitor C1. This base point is connected via a further switch S2$c$ to the base points of second and third capacitors C2 and C3 and to the negative pole of the reference voltage Vref. The positive poles of the reference voltage Vref and the center voltage Vm are connected to one another.

The probe terminal Vs+ is connected via a switch S1a to the capacitor C1. A switch S2b connects the capacitor C1 to the capacitor C2 and to the input of a second decoupling amplifier V2 whose output is connected to the inverting input D− of a difference amplifier D. A switch S2a connects the capacitor C1 to a third capacitor C3 and to the input of a first decoupling amplifier V1 whose output is connected to the noninverting [lacuna] D+ of the difference amplifier D.

The output of the difference amplifier D is connected to the positive pole of the center voltage Vm via an RC element composed of a resistor R7 and a capacitor C5.

A series circuit composed of a resistor R4 and a switch S3b is connected between the positive pole of the supply voltage Vcc (+5 V) and the input of the second decoupling amplifier V2, and the second capacitor C2. The resistor R4 is connected via a further switch S3a to the input of the first decoupling amplifier V1 and to the third capacitor C3.

A voltage divider composed of two resistors R5 and R6 of equal magnitude is arranged between the outputs of the two decoupling amplifiers V1 and V2, the tap of said voltage divider being connected on the one hand to the positive pole of the center voltage Vm via a fourth capacitor C4, and on the other hand directly to the noninverting input R+ of a controller R. The inverting input R− of the controller R is connected to the positive pole of the center voltage Vm, and its output is connected to the fourth probe terminal Rc.

Figure 3:
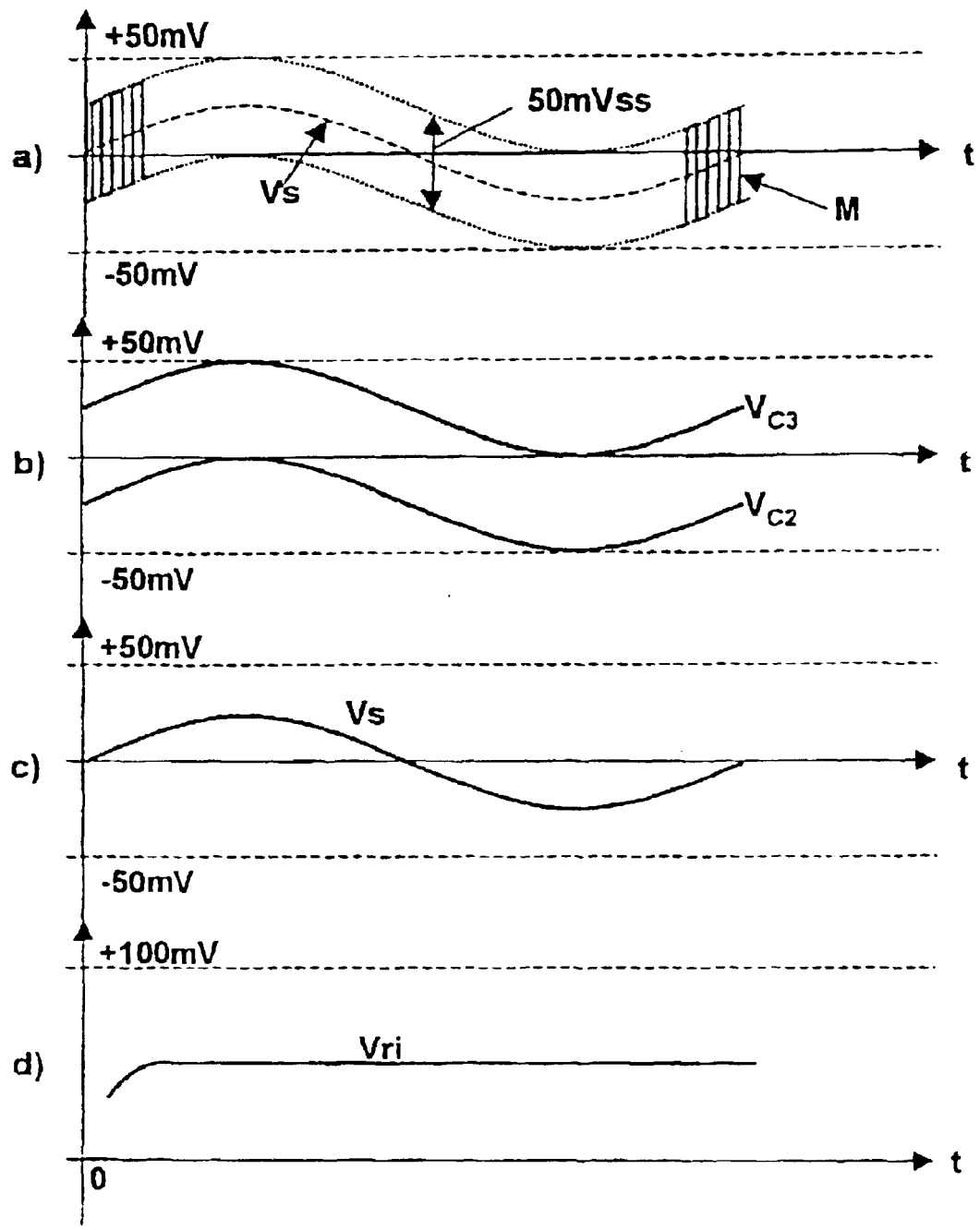
FIG. 3 shows a diagram which represents the acquisition of the Nernst voltage Vs and the voltage Vri representing the internal resistance Ris, from the sum voltage Vsum of the Nernst voltage Vs and the square wave voltage Vr.
Figure 4:
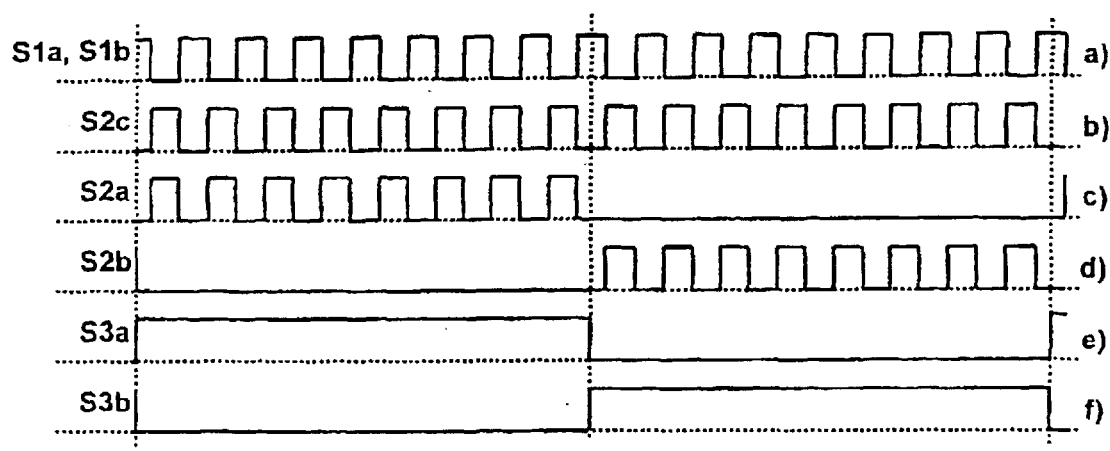
FIG. 4 shows a diagram of the control signals for the actuation of the switch.

The sum voltage Vsum composed of the Nernst voltage Vs and the square wave voltage Vr which drops across the internal resistor Ris of the probe and is brought about by the measurement signal M can be tapped at the probe terminal Vs+, said voltage Vr being illustrated in FIG. 3a. The voltages in FIGS. 3a to 3c are each referred to the positive potential of Vm (abscissa), and the center voltage Vm (=2.5 V) itself is not illustrated.

The Nernst voltage Vs will be assumed to have (as a theoretical example) a sinusoidal profile—as a control error caused by changes in the lambda value—with a very low frequency (approximately 50 Hz) and an amplitude of 50 mVss; the measurement signal M will be assumed to be a current of 500 μAss with a square wave profile and a frequency of 3 kHz, as already stated, which brings about, at the internal resistor Ris of the probe, a square wave voltage Vr of 500 μAss*100 Ω=50 mVss. The Nernst voltage Vs corresponds precisely to the mean value between the upper value OW and the lower value UW of the sum voltage Vsum (=Vr+Vs, FIG. 3a). The method for determining the Nernst voltage Vs and the internal resistance Ris of the probe from the sum voltage Vsum and by generating an oxygen reference current Icp will be explained in more detail below.

The determination of the Nernst voltage Vs from the sum voltage Vsum:

The sum voltage Vsum of the Nernst voltage Vs and the square wave voltage Vr superimposed on it is present at the switches S1a and S1b. The switches S1a and S1b are closed and opened alternately in synchronism, specifically with the frequency f (48 kHz), see 4a, and with a switch-on duration of 50% (i.e. the switch-on and switch off duration are of equal length). If the sum voltage Vsum is at its upper value OW, the first capacitor C1 is charged to this value when the switches S1a and S1b are closed.

If the switches S1a and S1b are then opened and the switches S2a and S2c are closed, a charge equalization takes place between the first capacitor C1 and the third capacitor C3. If these operations are repeated several times, the sum voltage Vsum is at its upper value OW (FIGS. 4a, 4b, 4c and 4e), the voltage at the third capacitor C3 reaches the instantaneous upper value OW of the sum voltage Vsum. The voltage $V_{C3}$ at the third capacitor C3 therefore follows the upper value OW of the sum voltage Vsum (FIG. 3b).

As long as the sum voltage Vsum is then at its lower value UW, the voltage present at the third capacitor C3 remains stored. In this time, the second capacitor C2 is charged to the lower value UW ($V_{C2}$) of the sum voltage Vsum by alternately actuating the switches S1a–S1b and S2b–S2c in an analogous fashion; said lower value UW ($V_{C2}$) is stored as long as the sum voltage Vsum is at its upper value OW (FIGS. 4a, 4b, 4d and 4e). The voltage $V_{C2}$ at the second capacitor C2 therefore follows the lower value UW of the sum voltage Vsum (FIG. 3b).

In order to avoid the capacitors C2 and C3 discharging during the storage phase, the decoupling amplifiers V1 and V2 with a gain factor one are connected downstream of them, in each case the same voltage being present at their outputs as at the second capacitor C2 or at the third capacitor C3.

The Nernst voltage Vs (FIG. 3c) which is located in the center between the upper and lower values of the sum voltage Vsum (FIG. 3a), referred to the center voltage Vm if the base points of the capacitors C2 and C3 were at the center voltage Vm, would be obtained at the tap of the voltage divider composed of the two resistors R5 and R6 which are of equal magnitude and are arranged between the outputs of the two decoupling amplifiers V1 and V2.

However, the controller R requires the difference ΔVs between the Nernst voltage Vs and reference voltage Vref. Owing to the connection of the center voltage Vm and the reference voltage Vref to their positive poles, the base points of the capacitors C2 and C3 are, however, at a potential which corresponds to the difference Vm−Vref between the center voltage Vm and reference voltage Vref so that the difference ΔVs=Vs−Vref already appears at the tap of the voltage divider R5-R6 and is fed to the noninverting input R+ of the controller R. If necessary, it is possible to smooth this voltage using the capacitor C4.

The controller R compares this signal with the center voltage Vm present at its inverting input. As a consequence of any deviation ΔVs−Vm, the controller R generates an output voltage which differs from the center voltage Vm. This output voltage is fed via the parallel circuit of the resistors Rc and Rp to the inverting input P+ of the pump current source P whose noninverting input P− is in turn connected to Vm. The pump electrodes of the probe which are located between the terminals Vp+ and Vp−/Vs− are also connected to the inverting input and the output of the pump current source.

The pump current source P will then attempt, by changing its output voltage, to adjust the voltage difference between its inverting and noninverting input to zero.

If the controller R then generates an output voltage which is different from Vm, the voltage at the inverting input of the pump current source would follow this; it would be unequal to Vm. The pump current source P therefore adjusts its output voltage in such a way that a current Ip is generated across the probe terminals Vp+ and Vp−/Vs−. This current also flows through the parallel circuit of the resistors Rc and Rp and generates a voltage drop there, which corresponds to the difference between the controller output voltage and Vm. As a result, the voltage Vm is in turn obtained at the inverting input P− of the pump current source P.

If the inputs of the amplifier IS are then connected to the parallel circuit of Rc and Rp, this current Ip can be measured very precisely as a voltage drop V(Ip) at the resistors Rc‖Rp. In this way, a voltage V(Ip) which is proportional to the pump current Ip—and thus to the lambda value of the exhaust gas—is obtained.

The voltage $V_{C3}$ at the third capacitor C3 is: $V_{C3}$=Vm=Vref+Vs+25 mV (of Vr).

The voltage $V_{C2}$ at the second capacitor C2 is: $V_{C2}$=Vm=Vref+Vs−25 mV (of Vr).

In the steady control state (Vs=Vref), the voltage at the third capacitor C3 is accordingly $V_{C3}$=Vm+25 mV, and at the second capacitor C2 is then correspondingly $V_{C2}$=Vm−25 mV; and ΔVs=0.

Determination of the internal resistance Ris of the probe from the sum signal Vsum:

As already described, the measurement signal M (500 μAss) is fed to the lambda probe S. As a result of this alternating current, a square wave voltage Vr of 500 μAss*Ris=500 μAss*100 Ω=50 mVss=±25 mV which is dependent on the instantaneous value of the internal resistor Ris of the probe (which will for example be assumed to be 100 Ω at the particular time) drops across the internal resistor Ris of the probe. This voltage corresponds to the difference $V_{C3}$-$V_{C2}$ of the output voltages of the two decoupling amplifiers V1 and V2 and is formed in the difference amplifier D. It can be used, after filtering by means of the RC element R7-C4, as a "temperature measuring voltage" Vri for regulating the probe temperature (FIG. 3d).

Generation of an oxygen reference current Icp:

A number of lambda probes require an artificial (pumped) oxygen reference to operate. This can be generated by pumping oxygen from the measuring cell of the positive reference electrode Vs+ by means of a small current Icp (for example 25 μA). The oxygen concentration which is produced as a result at the reference electrode is then used itself as a reference for measuring the oxygen concentration in the measuring cell. The evaluation circuit then has to make this current available.

Due to the pump current Ip, the voltage at the probe terminal Vp−/Vs− fluctuates between 0.5 V and 4.5 V. Owing to the Nernst voltage Vs, the voltage at the terminal Vs+ is 450 mV higher; it therefore fluctuates between 0.95 V and 4.95 V.

An oxygen reference current Icp was previously generated using a power source whose supply voltage was above 5 V, for example at 8 V. This voltage is either acquired from the battery voltage (12 V) using an additional controller, or from the 5 V supply voltage Vcc by means of a charge pump with an additional stabilizing means.

The aforementioned circuit fails when the battery voltage is low (Vbatmin=6 V), and the second circuit requires an additional degree of expenditure on circuitry associated with the risk of faults as a result of the switching operations of the charge pump.

The circuit according to the invention avoids this problem while at the same time requiring a minimum degree of additional expenditure on circuitry. It is composed of the resistor R4 and the two switches S3a and S3b. The switch S3a switches in synchronism with the positive amplitude of the square wave voltage Vr (3 kHz); switch S3b switches in antiphase to this—in synchronism with the negative amplitude of the square wave voltage Vr.

As described above, the voltage $V_{C2}$=Vm−25 mV is present at the second capacitor C2, and the voltage $V_{C3}$=Vm+25 mV is present at the third capacitor C3. Both voltages are therefore extremely close to Vm. If the resistor R4 (for example 100 kΩ (present at the supply voltage Vcc=5 V is then connected to the third capacitor C3 via switch S3a or to the second capacitor C2 via switch S3b, when the switches are conductive a current Icp will flow: Icp=(Vcc−Vm)/100 kOhm=25 μA).

Due to the switching of the switches S3a and S3b, this current is always fed to that capacitor of the capacitors C2 and C3 which is following the sum voltage Vsum at that particular time. Said current builds up a charge there. If the upper value OW of the sum voltage Vsum is present, switch S3a is closed and the current Icp flows into the capacitor C3. If the lower value UW of the sum voltage Vsum is present, switch S3b is closed and the current Icp flows into the capacitor C2.

The capacitor which is respectively in the storage phase is not connected to the resistor R4 so that there is no falsification of the stored voltage value by this current.

The capacitors C2 and C3 are alternately connected to the capacitor C1 as a result of the rapid switching of the switches S2a, S2b, S2c (FIG. 4) so that a continuous exchange of charges takes place. As a result, the current Icp—25 μA is also fed into the capacitor C1 via the resistor R4, and on through the switches S1a and S1b to the terminals Vs− and Vs+ of the lambda probe S. In this case, the switched capacitor C1 is used in the reverse direction to supply energy for the generation of the oxygen reference current Icp.

As a result of the simultaneously opened switches S3a and S3b, the oxygen reference current Icp can be interrupted. This may be necessary, for example, during the heating phase of the lambda probe S.

The current Icp is very stable and easy to generate as a result of the approximately constant voltage conditions at the resistor R4.

Figure 5:
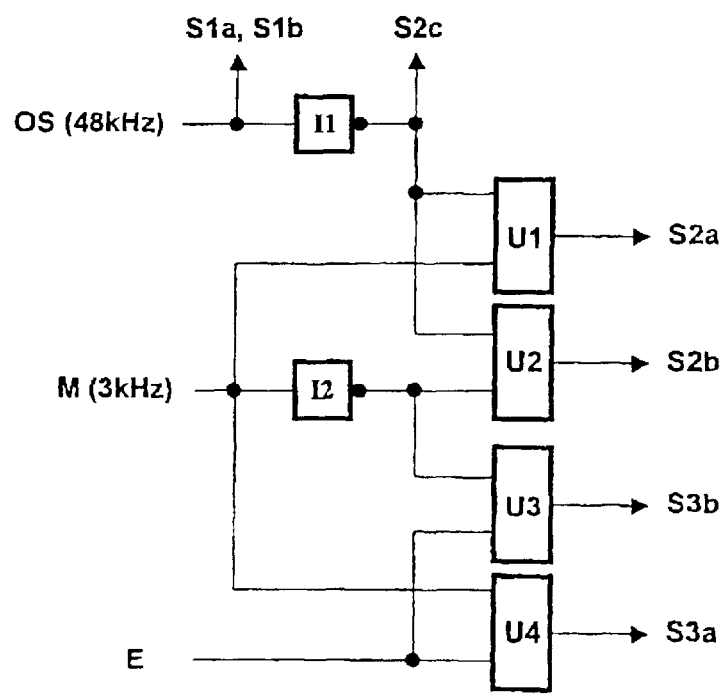
FIG. 5 shows a circuit for generating the control signals for actuation of the switch.

FIG. 5 shows a possible exemplary embodiment of a circuit which is located in the oscillator OSZ (FIG. 2) and has the purpose of generating the actuation signals for the switches S1a, S1b, S2a, S2b, S2c, S3a and S3b, which are electronic switches.

The drive signals for the switches are formed from the (square wave alternating current) oscillator signal OS which is formed in the oscillator OSZ and has the frequency f=$2^x$*fm (for example 48 kHz) and the signal M which is acquired by frequency division and has the frequency fm (3 kHz), as well as a permission signal E. The phase angle between these signals OS and M will be assumed to be such here that the signal M in the center of the low level goes from OS to high level (90° phase shift), see FIGS. 4b and 4e.

The switches S1a and S1b are driven in synchronism with the oscillator signal OS (FIGS. 4a, 5); the switch S2c is driven using the oscillator signal OS which is inverted by means of an inverter I1 (FIG. 4b). The three switches S1a, S1b and S2c are driven continuously.

The measurement signal M whose profile is similar to the drive signal for the switch S3a (FIG. 4e), and the drive signal for the switch S2c are fed to an AND element U1 whose output signal is the drive signal for switch S2a.

The measurement signal M which is inverted by means of an inverter I2, and the drive signal for the switch S2c are fed to an AND element U2 whose output signal is the drive signal for switch S2b.

The measurement signal M is fed to an input of an AND element U4, and the inverted measurement signal M is fed to an input of an AND element U3. The respective other input of the AND elements U3 and U4 is supplied with a permission signal E by means of which the output signals of these two AND elements, i.e. the drive signals of the switches S3a and S3b which are required to generate the oxygen reference current Icp are transmitted (E=high) or blocked (E=low), as already stated above.

Figure 6:
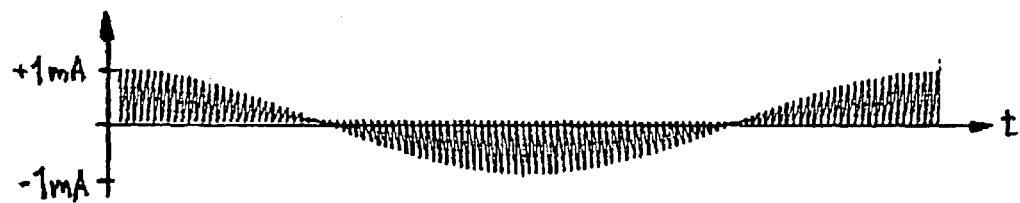
FIG. 6 shows the residual error of the unfiltered differential signal.

The device according to the invention for operating a linear lambda probe fulfills all the requirements mentioned at the beginning with a minimum degree of expenditure on circuitry: the measurement of the pump current Ip is carried out without common mode operation and therefore more precisely than has been possible hitherto; the decoupling of the Nernst voltage Vs and square wave voltage Vr is significantly more successful than hitherto, the Nernst voltage Vs showing virtually no residues of the square wave voltage Vr; the attenuation of the square wave voltage Vr in the Nernst voltage Vs being approximately 34 dB, to be precise without a phase shift. As a result, effects on the pump current control loop are avoided; the unfiltered error signal ΔVs (between the resistors R5 and R6 in FIG. 2) shows minimum residues of the square wave voltage Vr which are illustrated in FIG. 6, which however virtually disappear after filtering using the capacitor C4; the measurement of the internal resistance Ris of the probe is precise and not sensitive to interference influences; it does not exhibit any effects of the Nernst voltage Vs after smoothing using the Rc element R7-C5 (FIG. 2); the generation of the oxygen reference current Icp is very stable and is not dependent on the common mode signal of the probe; the circuit requires only a single supply voltage Vcc (5 V) and is very well suited for integration into an ASIC; and the successful decoupling of the Nernst voltage Vs and square wave voltage Vr makes the circuit according to the invention suitable for high speed lambda measurements such as are necessary for the operation of HPDI engines.

What is claimed is:

1. A device for operating a linear lambda probe of an internal combustion engine, comprising:

an evaluation circuit which is connected to the lambda probe via its terminals, an oscillator which generates an oscillator signal having a frequency, and a measurement signal which is derived therefrom by means of frequency division and has a relatively low frequency which is fed to a first probe terminal, a first difference amplifier whose inverting input is connected to a third probe terminal and whose noninverting input is connected to a fourth probe terminal, a controller and a pump current source, a first capacitor in which a lower value of the sum voltage is continuously stored is provided, a second capacitor in which an upper value of the sum voltage is continuously stored is provided, a base point of the first and second capacitors being capable of being connected to a second probe terminal and being connected to a negative pole of a reference voltage, a positive pole of the reference voltage being connected to a positive pole of a center voltage, a decoupling amplifier is connected downstream of each of the other terminals of the first and second capacitors, wherein the outputs of the two decoupling amplifiers are connected to one another by means of a voltage divider whose tap is connected to a noninverting input of the controller, whose output is connected to the fourth probe terminal, and whose inverting input lies at the center voltage and is connected to the noninverting input of the pump current source, an inverting input of the pump current source is connected to the third probe terminal, and the output of the pump current source is connected to the second probe terminal.

2. The device as claimed in claim 1, wherein a second difference amplifier is provided whose noninverting input is connected to the output of a first decoupling amplifier, whose inverting input is connected to the output of a second decoupling amplifier, and at whose output a temperature measuring voltage can be tapped.

3. The device as claimed in claim 2, wherein a low-pass filter is connected downstream of the second difference amplifier.

4. The device as claimed in claim 1, wherein a third capacitor whose base point is connected to the second probe terminal via a switch, and to the base points of the first capacitor and second capacitor via a further switch, and whose other terminal is connected to the first probe terminal via a switch, to the other terminal of the first capacitor via a switch, and to the other terminal of the second capacitor via a switch.

5. The device as claimed in claim 4, wherein a switch is provided via which a predefined oxygen reference current can be fed to the first capacitor, and to a reference cell of the lambda probe via said first capacitor and the third capacitor, as long as the sum voltage is at its upper value, and wherein a switch is provided via which the predefined oxygen reference current can be fed to the second capacitor, and to the reference cell of the lambda probe via said second capacitor and the third capacitor, as long as the sum voltage is at its lower value.

6. The device as claimed in claim 4, wherein a circuit is provided for actuating the switches, which circuit alternately connects, with the frequency of the oscillator signal, the third capacitor to a reference cell of the lambda probe via the switches, and to the second capacitor via the switches, as long as the sum voltage is at its upper value, and to the reference cell of the lambda probe via the switches, and to the first capacitor via the switches, as long as the sum voltage is at its lower value.

7. A method for operating a linear lambda probe having a first terminal, a second terminal, a third terminal, and a fourth terminal, comprising the steps of:

generating a current with a square-wave profile and relatively low frequency from an oscillator signal with a frequency, supplying the current at the first terminal as a measurement signal, tapping a sum voltage between the first and second terminals, whose upper and lower envelopes determine an upper value and a lower value, referring the sum voltage to the difference of a predefined center voltage and a predefined reference voltage, forming a mean value corresponding to the difference between a Nernst voltage and reference voltage from the upper value and lower value of the sum voltage, and converting the mean value into a proportional pump current which brings about, at a calibration resistor of the lambda probe, a voltage drop which is used as a measure of oxygen concentration.

8. The method as claimed in claim 7, wherein the step of generating the current is performed by means of frequency division.

9. The method as claimed in claim 7, wherein the difference between the upper value and lower value of the sum voltage is formed and is used as a temperature measuring voltage for regulating the temperature of the probe.

10. The method as claimed in claim 9, wherein the temperature measuring voltage is low-pass filtered.

11. The method as claimed in claim 7, wherein a predefined oxygen reference current can be fed to a reference cell of the lambda probe.

12. A method for operating a linear lambda probe of an internal combustion engine, the probe having a first terminal, a second terminal, a third terminal, and a fourth terminal, comprising the steps of:

deriving, from an oscillator signal with a frequency, by means of frequency division, a current having a square-wave profile and relatively low frequency;

supplying, as a measurement signal, the current at the first terminal thereby producing a square-wave voltage which drops across an internal resistor of the probe and forms, with a Nernst voltage tapped between the first and second terminals, a sum voltage whose upper and lower envelopes determine an upper value and a lower value;

referencing the sum voltage to a difference between a predefined center voltage and a predefined reference voltage;

forming a mean value corresponding to a difference between the Nernst voltage and reference voltage from the upper value and lower value of the sum voltage; and converting the mean value into a proportional pump current which brings about a voltage drop at a calibration resistor of the probe which is used as a measure of oxygen concentration in exhaust gas of the internal combustion engine.

13. The method as claimed in claim 12 further comprising:

forming the difference between the upper value and lower value of the sum voltage; and using the difference as a temperature measuring voltage for regulating probe temperature.

14. The method as claimed in claim 13, further comprising filtering the temperature measuring voltage through a low-pass filter.

15. The method as claimed in claim 12, further comprising feeding a predefined oxygen reference current to the reference cell of the lambda probe.

* * * * *